(12) United States Patent
Rodgers

(10) Patent No.: US 7,192,410 B1
(45) Date of Patent: Mar. 20, 2007

(54) ORTHOPEDIC REHABILITATION MECHANISM

(76) Inventor: Darell E. Rodgers, 705 Falling Leaf Dr., Friendswood, TX (US) 77546

( * ) Notice: Subject to any disclaimer, the term of this patent is extended or adjusted under 35 U.S.C. 154(b) by 0 days.

(21) Appl. No.: 10/860,623

(22) Filed: Jun. 2, 2004

Related U.S. Application Data

(60) Provisional application No. 60/475,176, filed on Jun. 2, 2003.

(51) Int. Cl.
*A61F 5/00* (2006.01)
*A63B 23/08* (2006.01)

(52) U.S. Cl. ............................. 602/36; 602/32; 482/79

(58) Field of Classification Search ............... 602/28, 602/40, 23, 27, 62, 16, 31; 482/79, 112, 482/51; 135/77–82, 84, 86, 69
See application file for complete search history.

(56) References Cited

U.S. PATENT DOCUMENTS

| | | | |
|---|---|---|---|
| 874,446 A * | 12/1907 | Slater ........................... | 602/23 |
| 1,509,793 A | 9/1924 | Thompson | |
| 1,573,296 A * | 2/1926 | Brasell ......................... | 602/23 |
| 1,577,712 A * | 3/1926 | Graham ........................ | 602/23 |
| 1,663,921 A * | 3/1928 | Pierce .......................... | 602/40 |
| 2,024,325 A * | 12/1935 | Allen ........................... | 602/23 |
| 2,198,908 A * | 4/1940 | Ellis ............................. | 602/40 |
| 2,206,902 A | 7/1940 | Kost | |
| 2,467,943 A | 4/1949 | Mikell, Jr. | |
| 2,830,816 A | 4/1958 | Uhl | |
| 4,186,920 A | 2/1980 | Fiore et al. | |
| 4,199,137 A | 4/1980 | Giguere | |
| 4,306,714 A | 12/1981 | Loomis et al. | |
| 4,371,161 A | 2/1983 | Williams | |
| 4,452,447 A | 6/1984 | Lepley et al. | |
| 4,602,627 A * | 7/1986 | Vito et al. ..................... | 602/23 |
| 4,650,183 A | 3/1987 | McIntyre | |
| 4,653,748 A | 3/1987 | Seel et al. | |
| 4,728,103 A * | 3/1988 | Fulton ......................... | 482/125 |
| 4,807,874 A | 2/1989 | Little | |
| 4,998,722 A | 3/1991 | Scott | |
| 5,100,129 A | 3/1992 | Porter et al. | |
| 5,186,698 A | 2/1993 | Mason et al. | |
| 5,215,508 A | 6/1993 | Bastow | |
| 5,256,119 A * | 10/1993 | Tudor ........................... | 482/74 |
| 5,368,536 A | 11/1994 | Stodgell | |
| 5,722,919 A * | 3/1998 | Timmer ........................ | 482/79 |
| 5,749,668 A | 5/1998 | McIlvain et al. | |
| 6,063,013 A | 5/2000 | Vathappallil | |
| 6,206,807 B1 | 3/2001 | Cowans et al. | |
| 6,361,517 B1 * | 3/2002 | Slinger ......................... | 602/28 |
| 6,368,258 B1 * | 4/2002 | Emlaw ......................... | 482/124 |
| 6,450,930 B1 * | 9/2002 | Kroke .......................... | 482/121 |
| 6,726,642 B2 * | 4/2004 | Danielsson et al. ............ | 602/5 |

\* cited by examiner

*Primary Examiner*—Henry Bennett
*Assistant Examiner*—Shumaya B. Ali

(57) ABSTRACT

The present invention provides an orthopedic device for therapy and rehabilitation of joints to increase the range of motion of the joint, a method of manufacture therefor, and a method of operating the same. The orthopedic device, among other possible elements, may include a foot support element configured to substantially support a user's foot or ankle, at least two guide lines each having a first and a second end, wherein each of the first ends are coupleable to the foot support element. The orthopedic device, may further include a control member coupleable to each of the second ends, the control member configured to control the at least two guide lines to flex the user's foot or ankle in a plurality of directions.

26 Claims, 4 Drawing Sheets

ORTHOPEDIC REHABILITATION MECHANISM

CROSS-REFERENCE TO PROVISIONAL APPLICATION

This application claims the benefit of U.S. Provisional Application No. 60/475,176 entitled "ANKLE RECOVERY MECHANISM ARM)," to Darell E. Rodgers, filed on Jun. 2, 2003, which is commonly assigned with the present invention and incorporated herein by reference as if reproduced herein in its entirety.

TECHNICAL FIELD OF THE INVENTION

The present invention is directed, in general, to an orthopedic rehabilitation mechanism and, more specifically, to an orthopedic device for therapy and rehabilitation of joints to increase the range of motion of the joint, a method of manufacture therefor, and a method of operating the same.

BACKGROUND OF THE INVENTION

With improving technology and medical procedures, knee, hip, ankle and other orthopedic surgery has been greatly refined in the recent past, and is more widely available and performed every year. While surgical procedures and techniques have improved, post operative treatment typically includes prevention of unnecessary residual joint stiffness and focuses on achieving maximum functional range of motion as soon as possible.

In order to achieve optimal recovery, early assisted and active joint motion is generally encouraged. In the past, physical therapists, physicians, and clinical staff were often required to manually assist recovering patients in therapy movement of reconstructed joints and the like. Additionally, beforehand there has not been available a simple, safe, and reliable apparatus for encouraging and enabling early assisted and active joint motion by the patient.

Physical therapists have been known to use bed sheets tied around a patient's foot to induce ankle joint motion after surgery. Obviously, this is a time consuming, inefficient, and, at times, unsafe manner of accomplishing prompt rehabilitation of affected joints. As can be imagined, the unreliability of such makeshift therapy equipment tends to add to the cost of health care and discourages patients from continuing therapy on their own to improve their range of motion when not supervised by a professional therapist. The use of bed sheets and other previously available devices can also allow for uncontrolled movements, slippage, and the like which, in turn, can cause pain, injury, lack of confidence in the therapy, and less willingness to undertake such therapy.

Follow-up surgical repair work after ankle and other joint surgery are considered by some as a surgical complication, and risks associated with such postoperative surgery include anesthetic complications, wound dehiscence, infection, etc. While complications cannot be avoided in all instances, it is believed that most such complications occur in cases where assisted and active joint motion therapy was not aggressively undertaken. Consequently, a reliable and simple device which can be used by the patient to facilitate and increase postoperative flexion and range of motion exercise of affected joints is needed and has heretofore been unavailable in the industry. Additionally, while the above-described paragraphs discuss achieving maximum functional range of motion as soon as possible after a traumatic injury and ensuing surgery, equally important is achieving maximum functional range of motion for elder persons and diabetics.

Accordingly, what is needed is a simple, safe, and reliable orthopedic rehabilitation mechanism for therapy and rehabilitation of a joint which has undergone reconstruction, prosthesis implant, orthopedic surgery, degradation because of age or diabetes, or the like that does not have the drawbacks of the prior art devices.

SUMMARY OF THE INVENTION

To address the above-discussed deficiencies of the prior art, the present invention provides an orthopedic device for therapy and rehabilitation of joints, a method of manufacture therefor, and a method of operating the same. The orthopedic device, among other possible elements, may include a foot support element configured to substantially support a user's foot or ankle, at least two guide lines each having a first and a second end, wherein each of the first ends are coupleable to the foot support element. The orthopedic device, may further include a control member coupleable to each of the second ends, the control member configured to control the at least two guide lines to flex the user's foot or ankle in a plurality of directions.

As previously noted, the present invention further includes a method for operating an orthopedic device. The method for operating the orthopedic device includes securing a foot or ankle to a foot support element, the foot support element coupled to a control member, and pulling different locations of the control member relative to the foot support element, the at least two guide lines causing the foot support element to flex the ankle or foot in a dorsi flexion direction, plantar flexion direction, inversion direction, eversion direction or any combination thereof.

The foregoing has outlined preferred and alternative features of the present invention so that those skilled in the art may better understand the detailed description of the invention that follows. Additional features of the invention will be described hereinafter that form the subject of the claims of the invention. Those skilled in the art should appreciate that they can readily use the disclosed conception and specific embodiment as a basis for designing or modifying other structures for carrying out the same purposes of the present invention. Those skilled in the art should also realize that such equivalent constructions do not depart from the spirit and scope of the invention.

BRIEF DESCRIPTION OF THE DRAWINGS

The invention is best understood from the following detailed description when read with the accompanying FIGUREs. It is emphasized that in accordance with the standard practice in the industry, various features are not drawn to scale. In fact, the dimensions of the various features may be arbitrarily increased or reduced for clarity of discussion. Reference is now made to the following descriptions taken in conjunction with the accompanying drawings, in which.

DETAILED DESCRIPTION

Figure 1:
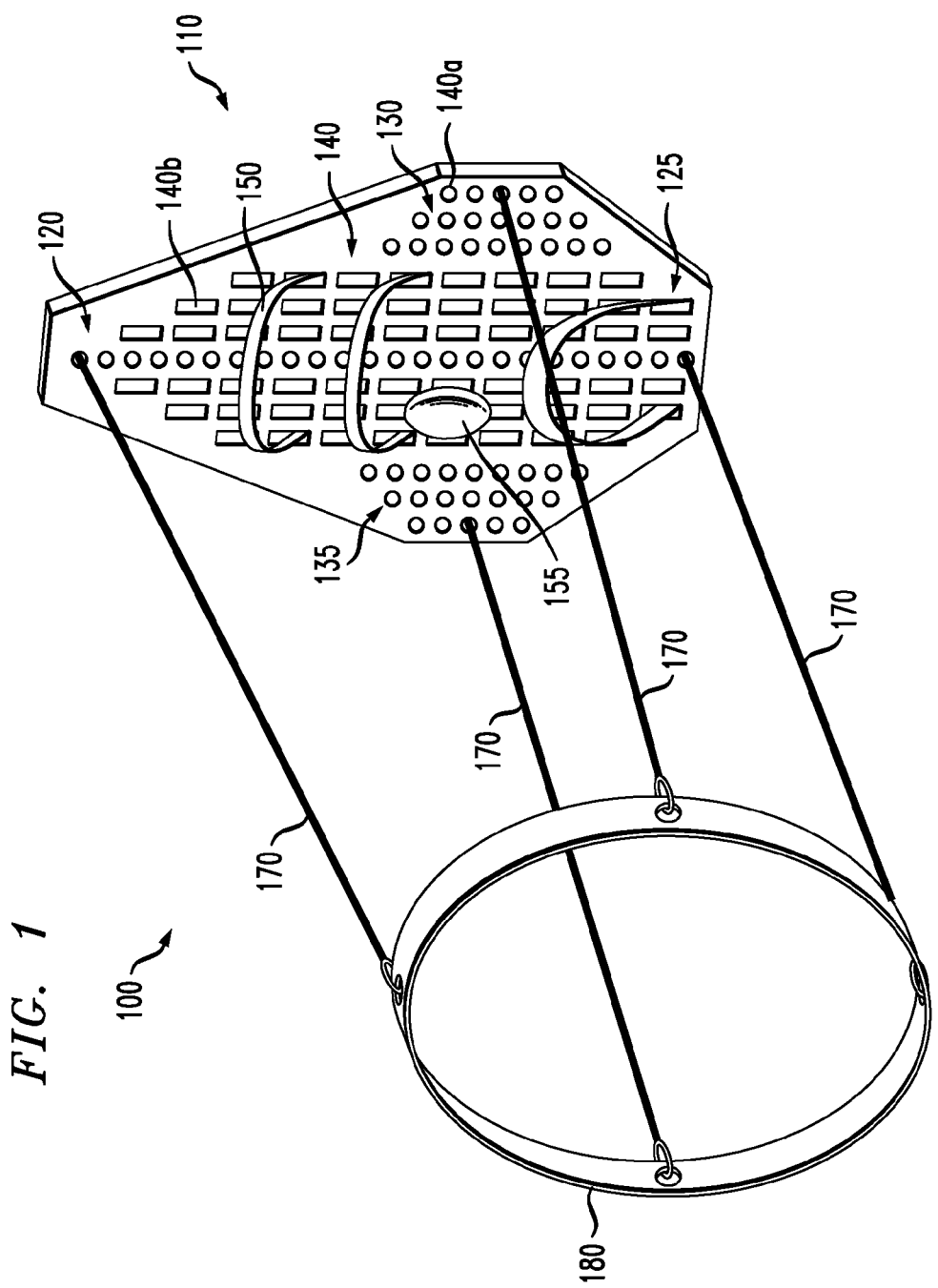
FIG. 1 illustrates a plan view of one embodiment of an orthopedic rehabilitation device.

Referring initially to FIG. 1, illustrated is a plan view of one embodiment of an orthopedic rehabilitation device 100. The orthopedic rehabilitation device 100 illustrated in FIG. 1, among other purposes, is designed to rehabilitate the bones, muscles, tendons and ligaments associated with a number of different joints. In an exemplary embodiment of the invention, however, the orthopedic rehabilitation device 100 is advantageously configured to rehabilitate the bones, muscles, tendons and ligaments associated with the ankle. Therefore, the orthopedic rehabilitation device 100 functions as an Ankle Recovery Mechanism (The ARM™).

The orthopedic rehabilitation device 100 illustrated in FIG. 1 initially includes a foot support element 110. The foot support element 110, as will be shown in subsequent figures, is designed to substantially support a user's foot or ankle. The foot support element 110 may comprise a number of different materials and shapes while remaining within the scope of the present invention. In one particular embodiment, the foot support element 110 comprises a substantially rigid material, such as hard plastic. Nevertheless, those skilled in the art understand that the foot support element 110 could comprise metal, resin, rubber, or any other substantially rigid material.

The foot support element 110, as dictated by its use, has a toe region 120, a heal region 125, an outer sole region 130 and an inner sole region 135. It should be noted that the depiction of which is the outer and inner sole region 130, 135, will vary depending on what foot, left or right, the device is affixed. In the current example, it is configured for the right foot. Depending on the shape of the foot support element 110, the aforementioned toe region 120, heal region 125, outer sole region 130 and inner sole region 135 may be interchanged. For instance, if the foot support element 110 were substantially square, a user's foot could be attached to the foot support element 110 in at least four different configurations. Nevertheless, in the embodiment of FIG. 1 the shape of the foot support element 110 is tapered, therefore the foot support element 110 may not accommodate different configurations as easily.

As is illustrated, the foot support element 110 includes a plurality of holes 140 located therein. The plurality of holes 140 have a number of different purposes. For instance, holes 140a are located proximate the toe region 120, heal region 125, outer sole region 130 and inner sole region 135 for accepting the guide lines 170. The plurality of holes 140a and their placement allow the positioning of the guide lines 170 to be tailored for a specific patient, or user. On the other hand, holes 140b are located proximate a position where the user's foot might be located. The holes 140b are configured to receive attachment means 150, such as support straps, to retain a user's foot or ankle within the foot support element 110. The plurality of holes 140b allow the attachment means 150 to be positioned to accommodate different size feet for the different user's that might use the orthopedic rehabilitation device 100.

Among other materials, the attachment means 150 may comprise any pliant or non-pliant material. In an exemplary embodiment of the invention a nylon strap having velcro on one or both ends would suffice as the attachment means 150. In an alternative embodiment, however, a stretchable bungy cord like material could be used as the attachment means 150. While only three attachment means are illustrated in FIG. 1, those skilled in the art appreciate that any combination of one or more attachments means 150 could be used.

Additionally, the attachment means 150 need not be a strap or a similar device. In certain embodiments it is envisioned where a boot is attached to or is the foot support element 110 for retaining the user's foot or ankle within the foot support element 110. The boot could be designed to fit a number of different foot sizes and could be coupled to the foot support element 110 using the aforementioned plurality of holes 140. Alternatively, the boot could be pre-fit to a given user's foot, thus being tailored to an individual user. As the pre-fit boot may be removably coupled to the foot support element 110, a number of different users having different pre-fit boots could each use the same orthopedic rehabilitation device 100.

In an exemplary embodiment, an arch support 155 is removably coupled to an upper surface of the foot support element 110. The arch support 155 is configured to provide support to an arch of the user during operation of the orthopedic rehabilitation device 100. As the arch support 155 is removably coupled to the foot support element 110, it can be removed if not needed, or positioned in a different location for a different user or foot. While illustrated, the arch support 155 is an option that may or may not be used.

Figure 2:
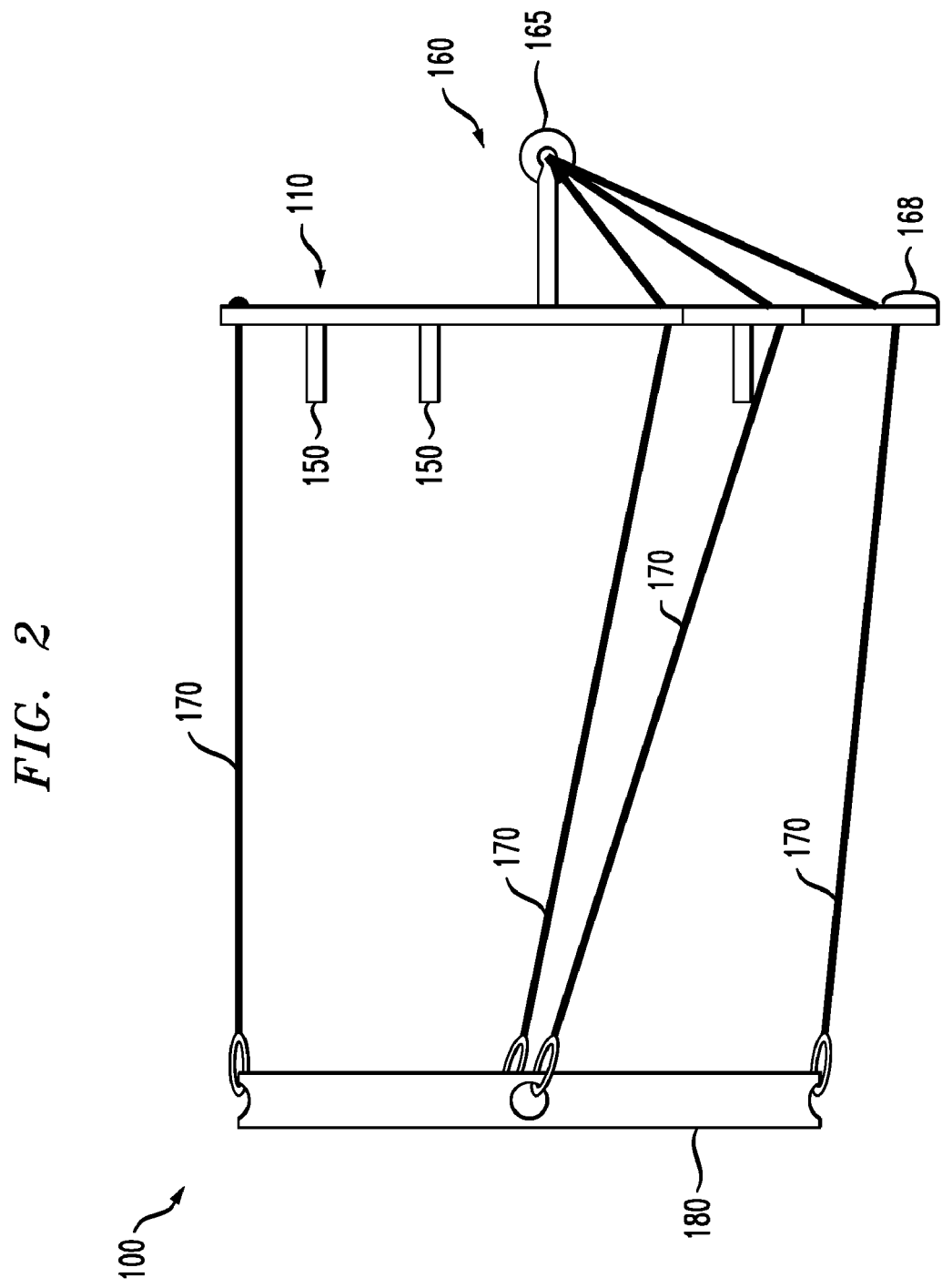
FIG. 2 illustrates a side view of the orthopedic rehabilitation device illustrated in FIG. 1.

Turning briefly to FIG. 2, illustrated is a side view of the orthopedic rehabilitation device 100 illustrated in FIG. 1. As is illustrated, a post portion 160 extends from a lower surface of the foot support element 110 in the embodiment of FIG. 2. The post portion 160 is configured to allow the user of the orthopedic rehabilitation device 100 to apply additional leverage to his or her foot or ankle during its use. In an exemplary embodiment the post portion 160 comprises a similar material as the foot support element 110, and contains a capping member 165 located on a distal surface thereof. The capping member 165 in the embodiment of FIG. 1 is designed to provide a connection point between the post portion 160 and the guide lines 170 (see below). It is also believed that the capping member 165 may allow the orthopedic rehabilitation device 100 to be operated on a slick surface, such as tile or wood, without a substantial concern that the post portion 160 would slip and further injure the user.

The post portion 160 may be movably coupled to the foot support element 110. For instance, the post portion 160 may be coupled to any one of the holes 140 of the foot support element 110. Depending on the desires of the user, the optimal position of the post portion 160 may change. These holes 140 further allow the position of the post portion 160 to be optimized. While it generally depends on the specific user, it is believed that the optimal position for the post portion 160 is centered on the user's foot.

In one advantageous embodiment, a number of the guide lines 170 extend through the holes 140a in the foot support element 110 and couple to the post portion 160 of the foot support element 110. While all of the guide lines 170 may couple to the post portion 160, the particular embodiment of FIG. 2 illustrates only the guide lines 170 that extend through the holes 140a of the heal region 125, outer sole region 130 and inner sole region 135 coupling to the post portion 160. Accordingly, the guide line 170 contacting the toe region 120 does not couple to the post portion 160. This configuration is designed to allow the user to further increase the aforementioned leverage.

Further located on a lower surface of the foot support element 110 in the embodiment of FIG. 2 is a sliding means 168. In the particular embodiment shown, the sliding means 168 is a tear shaped extension coupled to the heal region 125 of the foot support element 110. The sliding means 168, in one embodiment, is configured to allow the foot support element 110 to easily slide toward and away from the user when the heal region 125 of the foot support element 110 is resting on the floor and the user is working plantar and/or dorsi flexion.

The sliding means 168 may comprise a variety of different shapes and materials, if used, so long as it assists the heal region 125 of the foot support element 110 in sliding along the surface upon which it is being used. In one example, the sliding means 168 comprises a material providing very little friction, for instance hard plastic. Nevertheless, the prevent invention should not be limited so such. It should also be noted that the shape and location of the sliding means 168 may change. Above that shown in FIG. 2, it is envisioned where the sliding means 168 may extend from the lower surface of the foot support element 110 along the radial edge of the foot support element 110 and onto the upper surface of the foot support element 110. This embodiment would be useful for applications where the foot support element 110 is being used in a position substantially perpendicular to the floor.

Returning to FIG. 1, with continued reference to FIG. 2, the orthopedic rehabilitation device 100 further includes a control member 180. In the illustrative embodiment, the control member 180 has an opening therein and is configured to receive a user's leg therethrough. In the embodiment of FIG. 1 the control member 180 is a ring, or hoop, and is formed in the shape of a circle. Other shapes, including a triangle, square, or any three or more sided object could nevertheless be used. Additionally, the control member 180 need not form a closed circle. In an alternative embodiment, extension members could be coupled to the control member 180. The extension members might be configured in much the same way as a control member used to operate a child's puppet, for example in the shape of an X. Nevertheless, these extension members are not required.

In an alternative embodiment of the invention (not shown) the control member 180 does not receive the user's leg therethrough, and is just operated with the control member 180 proximate the user's mid-section or lap. While in this embodiment the control member 180 may still have an opening therein, such is not demanded as it does not need to accommodate the user's leg therethrough. Accordingly, the control member 180 of this embodiment may be a circular plate, a plate forming a polygon, a cross, a plus sign, or another similar shape while staying within the scope of the present invention.

Coupling the control member 180 to the foot support element 110 are at least two guide lines 170. While only two guide lines 170 are required, an exemplary embodiment has three or more guide lines 170 being used. For instance in the embodiment of FIG. 1 four guide lines 170 are being used. As is illustrated, a first end of each of the four guide lines 170 is coupled to the toe region 120, the heal region 125, the outer sole region 130 and the inner sole region 135, respectively, while the second end of each of the four guide lines 170 is coupled to various opposing locations of the control member 180.

In an exemplary embodiment the guide lines 170 comprise a rope like material. For instance, it is believed that the type of rope commonly used by rock climbers would work extremely well. Other materials, such as wire, chain, etc., could nonetheless be used for the guide lines 170. The length of the guide lines 170 may be adjusted depending on the height and comfortability of the user. Similarly, each of the at least two guide lines 170 need not be similar lengths. For example, depending on the height of the user, length of the leg of the user, and type and amount of Range Of Motion (ROM) that is desired, each of the at least two guide lines 170 may be individually either lengthened or shortened.

Figure 3:
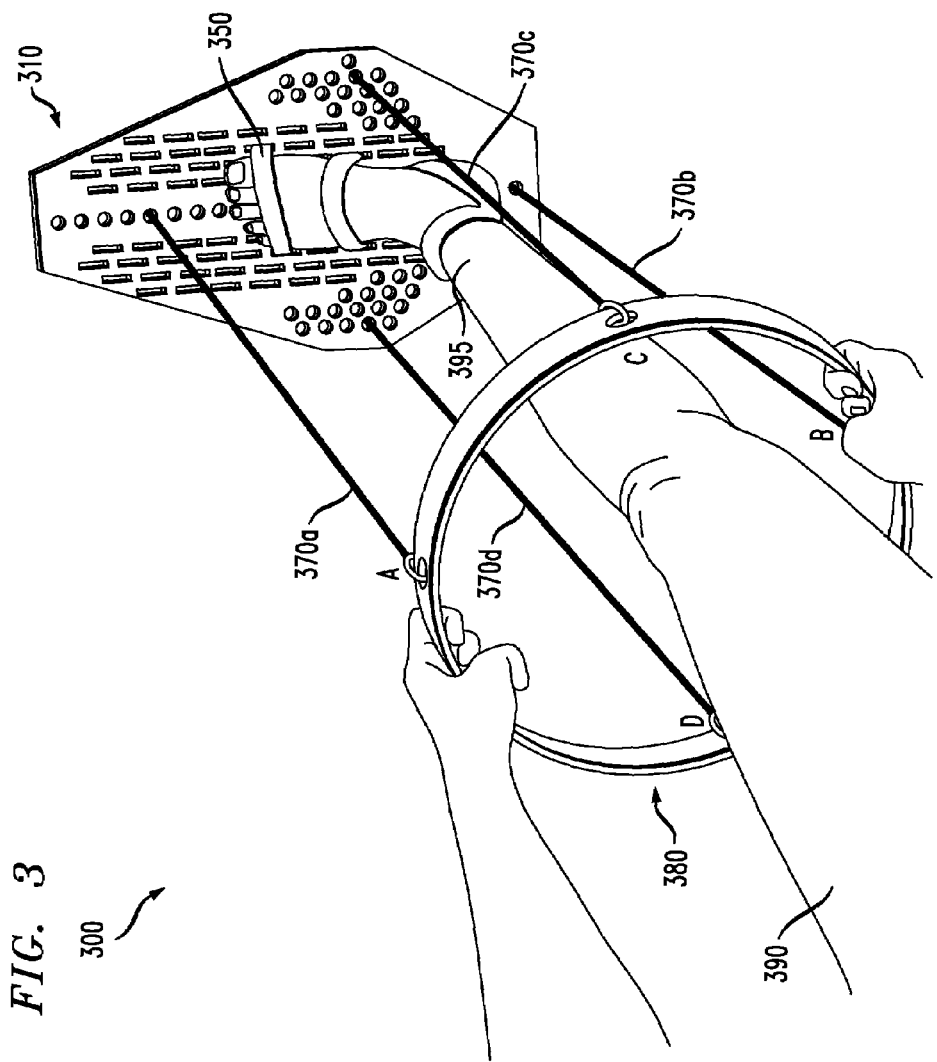
FIGS. 3–4 illustrate schematic views of the use of an orthopedic rehabilitation device manufactured according to the principles of the present invention.
Figure 4:
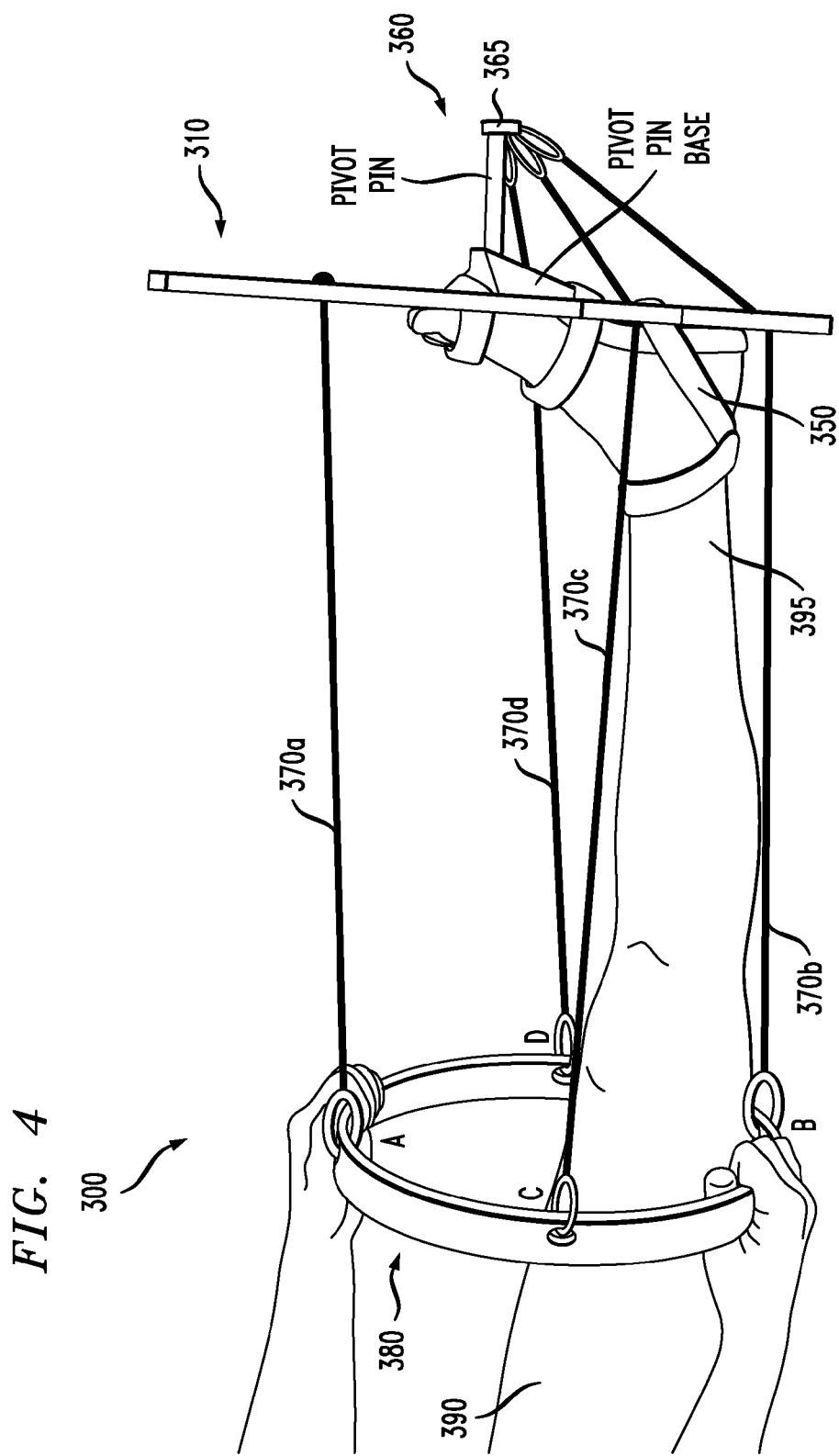

Turning now to FIGS. 3–4 illustrated are schematic views of the use of an orthopedic rehabilitation device 300 manufactured according to the principles of the present invention. In the embodiments illustrated in FIGS. 3–4, a user's leg 390, including the user's foot and ankle 395, is coupled to the orthopedic rehabilitation device 300 by way of the attachment means 350. While the embodiment illustrated in FIGS. 3–4 illustrates the user's left leg, left foot and ankle coupled to the orthopedic rehabilitation device 300, the orthopedic rehabilitation device 300 works equally as well for the right leg, foot and ankle.

The orthopedic rehabilitation device 300 is quite easy to use, however, it plays a huge impact in the rehabilitation of joints, and particularly the ankle joint. For example, by pulling point A of the control member 380 toward a torso of the user, the guide line 370*a* causes the foot support element to assist in dorsi flexion of the foot. In contrast, by pulling point B of the control member 380 toward a torso of the user, the guide line 370*b* causes the foot support element to assist in plantar flexion of the foot. Similarly, by pulling point C of the control member 380 toward a torso of the user, the guide line 370*c* causes the foot support element to assist in inversion of the foot. Lastly, by pulling point D of the control member 380 toward a torso of the user, the guide line 370*d* causes the foot support element to assist in eversion of the foot.

The embodiment discussed in the paragraph above assumes that a user's left leg is coupled to the foot support element 310. If the right leg, right foot and ankle were coupled to the foot support element 310 rather than the left leg as illustrated, guide line 370*c* would cause the foot support element 310 to assist in eversion of the foot. Similarly, if the right leg, right foot and ankle were coupled to the foot support element 310 rather than the left leg as illustrated, guide line 370*d* would cause the foot support element 310 to assist in inversion of the foot.

Those skilled in the art understand that the user could also pull a point in between say A and C (e.g, between any adjacent points) of the control member 380 toward a torso of the user, and the guide lines 370*a* and 370*c* would cause the foot support element 310 to simultaneously assist in both dorsi flexion and inversion (if using the left leg) of the foot. Accordingly, the orthopedic rehabilitation device 300 manufactured in accordance with the principles of the present invention can flex, and thus rehabilitate, the user's foot or ankle in a plurality of directions.

It should nonetheless be noted that while the embodiments of FIGS. 1–3 illustrate the control member having an opening therein configured to receive the user's leg, such is not always the case, as mentioned above. Similar, and possibly better flexibility may be attained by placing the control member in the user's lap during operation thereof. This method of operation may allow the user to apply even greater leverage to his or her foot or ankle during its use. Accordingly, as discussed above, the control member need not have an opening therein in all embodiments.

Normal mobility requires adequate tissue length and neuromuscular involvement. The structures involved in mobility and affected by the orthopedic rehabilitation device 100, without limitation, are joint articulation surfaces, joint capsule, tendons, ligaments, bursae, muscle, fascia, and skin. Normal motion is impaired when stiffening and/or shortening occur due to injury, adhesions, or immobilization. In order to regain normal motion, stretching of the stiff and/or short tissues must be done to increase ROM and/or guide healing tissues to proper length during the healing phases. While stretching and mobilizing stiff and/or shortened tissues has traditionally been restricted to manual therapy by a physical therapist, the orthopedic rehabilitation device 100 allows the patient to perform rigorous stretching in all pluralities of motion without the traditional hands-on physical therapy session. The orthopedic rehabilitation device 100 will stretch the affected tissues, which will stimulate fibrocytes to reestablish the tissue to the desired length. Elongation stimulates fibroblasts to lay collagen along the lines of stress produced by the manipulation of the orthopedic rehabilitation device, which will strengthen the tissue in the new lengthened position. Prevention of adhesions and contractures, decreased pain, evacuation of accumulated fluid, increased circulation, enhanced nutrition, decreased joint or tissue effusion, chondral repair, and early return of ROM are all associated benefits of stretching done with the orthopedic rehabilitation device 100. Further, not only will it benefit those having experienced a traumatic injury with or without an ensuing surgery, it is equally as applicable for elderly persons or diabetics with ROM problems. Additionally, it may be used for issues related to flat feet as well as simple or complex strains to the ligaments, tendons and muscles associated with the joints.

Although the present invention has been described in detail, those skilled in the art should understand that they can make various changes, substitutions and alterations herein without departing from the spirit and scope of the invention in its broadest form.

What is claimed is:

1. An orthopedic device for therapy and rehabilitation of joints, the device comprising:
   a foot support element configured to substantially support a user's foot or ankle;
   at least two flexible guide lines each having a first and a second end, wherein each of the first ends are coupleable to the foot support element; and
   a control member coupleable to each of the second ends, the control member configured to control the at least two guide lines and assist in movement of the user's foot or ankle in a dorsi flexion direction, plantar flexion direction, inversion direction, and eversion direction.

2. The orthopedic device as recited in claim 1 wherein the control member has an opening therein configured to receive a user's leg therethrough.

3. The orthopedic device as recited in claim 1 wherein the foot support element has a post portion extending from a lower surface thereof.

4. The orthopedic device as recited in claim 3 wherein each of the first ends extend through an opening in the foot support element and attach to the post portion.

5. The orthopedic device as recited in claim 3 wherein the post portion is movably coupled to a lower surface of the foot support element for adjustment thereto.

6. The orthopedic device as recited in claim 1 wherein the foot support element has a toe region, a heal region, an outer sole region and an inner sole region, and wherein each of the regions has a plurality of holes located therein for accepting the first ends.

7. The orthopedic device as recited in claim 1 wherein the foot support element has a plurality of holes located therein for accepting a support strap configured to retain a user's foot or ankle within the foot support element, the plurality of holes accommodating different size feet.

8. The orthopedic device as recited in claim 1 wherein the foot support element comprises a material selected from the group consisting of:
   metal;
   plastic;
   rubber; and
   resin.

9. The orthopedic device as recited in claim 1 wherein the control member is a ring.

10. The orthopedic device as recited in claim 9 wherein the ring has a shape selected from the group consisting of:
    triangular,
    square; and
    circular.

11. The orthopedic device as recited in claim 1 wherein the control member has a configuration selected from the group consisting of:
    a circular plate;
    a plate having a polygon shape;
    a cross; and
    a plus sign.

12. The orthopedic device as recited in claim 1 further including an arch support coupled to an upper surface of the foot support element.

13. The orthopedic device as recited in claim 1 wherein the foot support element is a boot, the at least two guidelines coupleable to the boot.

14. A method for manufacturing an orthopedic device for therapy and rehabilitation of joints, comprising:
    providing a foot support element for substantially supporting a users foot or ankle;
    providing at least two flexible guide lines each having a first and a second end, wherein each of the first ends are coupleable to the foot support element; and
    providing a control member coupleable to each of the second ends, the control member configured to control the at least two guide lines to assist in movement of the user's foot or ankle in a dorsi flexion direction, plantar flexion direction, inversion direction, and eversion direction.

15. The method as recited in claim 14 wherein the control member has an opening therein configured to receive a user's leg therethrough.

16. The method as recited in claim 14 further including coupling the first ends to the foot support element and coupling the second ends to the control member.

17. The method as recited in claim 14 wherein the foot support element has a post portion extending from a lower surface thereof.

18. The method as recited in claim 17 wherein each of the first ends extend through an opening in the foot support element and attach to the post portion.

19. The method as recited in claim 14 wherein the foot support element has a toe region, a heal region, an outer sole region and an inner sole region, and further including forming a plurality of holes within each of the regions for accepting the first ends.

20. The method as recited in claim 14 further including forming a plurality of holes within the foot support element for accepting a support strap configured to retain a user's foot or ankle within the foot support element, the plurality of holes accommodating different size feet.

21. The method as recited in claim 14 wherein the foot support element includes an arch support coupled to an upper surface thereof.

22. A method for operating an orthopedic device for therapy and rehabilitation of joints, comprising:
    securing a foot or ankle to a foot support element, the foot support element coupled to a control member using at least two flexible guide lines; and pulling different locations of the control member relative to the foot support element, the at least two flexible guide lines configured to cause the foot support element to flex the ankle or foot in a dorsi flexion direction, plantar flexion direction, inversion direction, and aversion direction.

23. The method as recited in claim 22 wherein the control member has an opening therein configured to receive a user's leg therethrough.

24. The orthopedic device as recited in claim 1 wherein the at least two flexible guide lines comprise a stretchable material.

25. The orthopedic device as recited in claim 1 wherein the control member is configured such that pulling thereon applies the force thereto.

26. The orthopedic device as recited in claim 1 wherein the control member is configured to control the at least two guide lines to assist in movement of the user's foot or ankle in any combination of the dorsi flexion direction, the plantar flexion direction, the inversion direction, and the aversion direction when a force is applied thereto.

* * * * *